United States Patent [19]

Urano et al.

[11] Patent Number: 5,220,055
[45] Date of Patent: Jun. 15, 1993

[54] PROCESS FOR PRODUCING AMINOCARBOXYLIC ACID SALTS

[75] Inventors: Yoshiaki Urano, Kawasaki; Yukio Kadono; Takakiyo Goto, both of Yokohama, all of Japan

[73] Assignee: Nippon Shokubai Co., Ltd., Osaka, Japan

[21] Appl. No.: 861,893

[22] PCT Filed: Oct. 21, 1991

[86] PCT No.: PCT/JP91/01440
§ 371 Date: Jun. 23, 1992
§ 102(e) Date: Jun. 23, 1992

[87] PCT Pub. No.: WO92/06949
PCT Pub. Date: Apr. 30, 1992

[30] Foreign Application Priority Data

Oct. 23, 1990 [JP] Japan ................... 2-286670

[51] Int. Cl.$^5$ .................. C07C 51/295; C07C 229/08
[52] U.S. Cl. ..................... 562/539; 562/526; 562/538
[58] Field of Search ............. 562/539, 538, 526, 531, 562/534

[56] References Cited

U.S. PATENT DOCUMENTS 3,833,650  9/1974  Schulze et al. ............... 562/526
3,842,081 10/1974  Schulze et al. ............... 562/526
4,782,183 11/1988  Goto et al. ................... 562/539 X

FOREIGN PATENT DOCUMENTS 60-41645   3/1985  Japan.
60-78948   5/1985  Japan.
60-97945   5/1985  Japan.
60-100545  6/1985  Japan.

Primary Examiner—Arthur C. Prescott
Attorney, Agent, or Firm—Sherman and Shalloway

[57] ABSTRACT

There is provided a novel process for producing aminocarboxylic acid salts useful as starting materials of agricultural chemicals and medicines, chelating agents, food additives, and so on. This process is characterized in that when producing an aminocarboxylic acid salt by an oxidative dehydrogenation reaction of an amino alcohol in the presence of an alkali metal hydroxide and/or an alkaline earth metal hydroxide, a copper-containing catalyst and water, the reaction is performed by adding an aluminum metal and/or an aluminum compound (e.g., sodium aluminate and aluminum hydroxide) to the reaction system.

3 Claims, No Drawings

PROCESS FOR PRODUCING AMINOCARBOXYLIC ACID SALTS

TECHNOLOGICAL FIELD

This invention relates to a novel process for producing aminocarboxylic acid salts useful as starting materials of agricultural chemicals and medicines, chelating agents, food additives, and so on.

TECHNOLOGICAL BACKGROUND

As an industrial process for producing aminocarboxylic acid salts, a Strecker process has been generally employed in which glycine salts, iminodiacetic acid salts or nitrilotriacetic acid salts are obtained using hydrocyanic acid and formaldehyde as starting materials. Since, however, hydrocyanic acid is a deadly poisonous gas, the process is greatly limited in production equipment, handling, location area, etc. Moreover, because hydrocyanic acid is mostly obtained as a byproduct in producing acrylonitrile, there has been a big problem in the aspect of securing safety of starting materials.

Also known is a process in which aminocarboxylic acid salts are produced by oxidatively dehydrogenating amino alcohols in alkali hydroxides (U.S. Pat. Nos. 2,384,816, 2,384,817, 3,535,373, 3,842,081 and 3,739,021, etc.) U.S. Pat. No. 2,384,816 discloses a process in which an amino alcohol is reacted with an alkali metal hydroxide in the absence of a catalyst. In this process, however, a reaction time is long and a yield of the aminocarboxylic acid salt is low. U.S. Pat. No. 2,384,817 discloses a process in which potassium glycinate is formed by anhydrously reacting monoethanolamine with potassium hydroxide in the presence of a copper catalyst. In this process, however, according to the present inventors' knowledge, a yield of the glycinate is not good. U.S. Pat. No. 3,578,709 discloses a process in which a nitrilotriacetic acid salt is formed by reacting triethanolamine with an alkali hydroxide in the presence of a zinc oxide catalyst. This process is, nevertheless, unsatisfactory in a yield of the nitrilotriacetic acid salt. U.S. Pat. No. 3,842,081 discloses that potassium iminodiacetate is obtained in a relatively high yield by reacting diethanolamine with potassium hydroxide in the presence of cadmium oxide. U.S. Pat. Nos. 3,535,373, 3,578,709 and 3,739,021 disclose that a nitrilotriacetic acid salt is formed by reacting triethanolamine with an alkali hydroxide in the presence of cadmium oxide. However, because of a risk of incorporating a poisonous cadmium compound into a reaction product, these processes using cadmium oxide as a catalyst cannot be used at all depending on the use and suffer a problem of waste matters; they cannot become a technology competitive with the Strecker process.

A process is further known in which an amino-carboxylic acid salt is obtained by reacting an amino alcohol in the presence of an alkali hydroxide, water and a copper-containing catalyst or a catalyst containing copper and zirconium (U.S. Pat. No. 4,782,183). In the process, selectivity to the aminocarboxylic acid salt is indeed as high as 95 %, but the repeated use of the catalyst tends to decrease selectivity and increase by-products. Main by-products are an oxalic acid salt when producing a glycine salt using monoethanolamine as a starting material, a glycine salt when producing an iminodiacetic acid salt using diethanolamine as a starting material, and an iminodiacetic acid salt and a glycine salt when producing a nitrilotriacetic acid salt using triethanolamine as a starting material. Accordingly, in order to obtain the aminocarboxylic acid with good selectivity, there is a need to exchange the catalyst for a short period of time or to recover the catalyst by a complex purification step.

It is an object of this invention to provide a novel process, which is free from a toxicological problem, which gives little by-products, which is high in yield and selectivity, which allows the repeated use of the catalyst, and which can therefore produce an aminocarboxylic acid salt economically advantageously.

DISCLOSURE OF THE INVENTION

The present inventors have made various investigations, in view of the aforesaid problems, on a process in which an aminocarboxylic acid salt is formed by oxidatively dehydrogenating an amino alcohol in the presence of a copper-containing catalyst, and consequently have found that when an aluminum metal and/or an aluminum compound is added to an oxidative dehydrogenation reaction system, it is effective for suppressing formation of by-products. Further extensive investigations have led to completion of this invention. Thus, according to this invention, there is provided a process for producing an aminocarboxylic acid salt by an oxidative dehydrogenation reaction of an amino alcohol represented by formula (1)

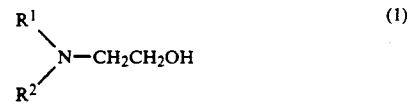

wherein $R^1$ and $R^2$, independently from each other, denote a hydrogen atom, a hydroxyethyl group, an alkyl group having 1 to 18 carbon atoms, or an aminoalkyl group having 2 to 3 carbon atoms, in the presence of an alkali metal hydroxide and/or an alkaline earth metal hydroxide, a copper-containing catalyst and water, characterized in that the reaction is carried out by adding an aluminum metal and/or an aluminum compound to the reaction system.

By the process of this invention, $CH_2OH$ of the amino alcohol represented by formula (1) is oxidatively dehydrogenated to $COOH$. In case $R^1$ and $R^2$ in formula (1) are hydroxyethyl groups, $CH_2OH$'s thereof are also oxidatively dehydrogenated to $COOH$'s; obtaining an aminocarboxylic acid salt containing plural $COOH$'s is also included in this invention.

Examples of the amino alcohol represented by formula (1) are monoethanolamine, diethanolamine, triethanolamine, N-methylethanolamine, N-ethylethanolamine, N-isopropylethanolamine, N-butylethanolamine, N-nonylethanolamine, N-(2-aminoethyl)ethanolamine, N-(3-aminopropyl)ethanolamine, N,N-dimethylethanolamine, N,N-diethylethanolamine, N,N-dibutylethanolamine, N-methyldiethanolamine, N-ethyldiethanolamine, N-isopropyldiethanolamine, N-butyldiethanolamine, N-ethyl-N-(2-aminoethyl)ethanolamine, and N-methyl-N-(3-aminopropyl)ethanolamine.

Using these aminoalcohols as a starting material, corresponding aminocarboxylic acid salts can be produced. Concrete examples of the aminocarboxylic acid are glycine, iminodiacetic acid, nitrilotriacetic acid, N-methylglycine, N-ethylglycine, N-isopropylglycine, N-butylglycine, N-nonylglycine, N-(2-aminoethyl)glycine, N-(3-aminopropyl)glycine, N,N-dimethylglycine, N,N-diethylglycine, N,N-dibutylglycine, N-methyliminodiacetic acid, N-ethyliminodiacetic acid, N-isopropyliminodiacetic acid, N-butyliminodiacetic acid, N-ethyl-N-(2-aminoethyl)glycine, and N-methyl-N-(3-aminopropyl)glycine. In the process of this invention, these aminocarboxylic acids are formed as alkali metal salts and/or alkaline earth metal salts.

The catalyst used in this invention contain copper as an essential component. As a copper source, metallic copper, copper oxide, copper hydroxide, copper inorganic salts such as copper nitrate, copper sulfate, copper carbonate and copper halides, and copper organic salts such as copper formate, copper acetate, copper propionate and copper lactate are available. The form of the catalyst is not particularly limited. For example, a catalyst obtained by oxidizing a surface of metallic copper and then reducing it with hydrogen, a catalyt obtained by developing Raney copper with an alkali aqueous solution, and activated copper obtained by thermally decomposing and/or reducing copper formate, copper carbonate, or the like can be used either as such or by supporting same on an alkali-resistant carrier. When the catalyst is used by supporting it on the alkali-resistant carrier, said catalyst can easily be separated from the reaction mixture after the reaction, with a result that it can easily be recovered and reused advantageously. Examples of the catalyst which is especially preferable in the aspects of its activity and life are developed Raney copper and a product obtained by supporting copper on zirconium oxide or silicon carbide by coprecipitation or impregnation. The amount of the catalyst used is 1 to 70% by weight, preferably 10 to 40% by weight based on the weight of the amino alcohol.

As the alkali metal hydroxide or the alkaline earth metal hydroxide used in this invention, sodium hydroxide, potassium hydroxide, etc. are especially preferable. They can be used in the form of a flake, a powder, pellets or an aqueous solution; the aqueous solution is preferable from the aspect of handling. The amount of the alkali metal hydroxide or the alkaline earth metal hydroxide is equivalent or more, preferably 1.0 to 2.0 equivalents based on the amount of the hydroxyl group of the amino alcohol used in the reaction.

Examples of the aluminum compound used in this invention are aluminum hydroxide, aluminic acid salts such as sodium aluminate and potassium aluminate, and aluminum halides such as aluminum chloride. In the aspects of handling and economy, sodium aluminate or aluminum hydroxide is preferably used. The amount of the aluminum metal and/or the aluminum compound is 0.001% by weight or more, as an aluminum atom, based on the weight of the amino alcohol, which is effective for suppressing by-products. Preferable is 0.002 to 0.5% by weight. When said amount exceeds 0.5% by weight, it is economically disadvantageous, though it does not adversely affect the yield of the aminocarboxylic acid salt.

By the way, in the process of this invention, after the reaction is finished, the catalyst can be separated and recovered from the reaction system and reused in the next reaction. On that occasion, in order to make up for the amount of the catalyst lost in the previous reaction or for the decreased activity, a required amount of a non-used catalyst may be added. Where the non-used catalyst contains an aluminum metal and/or an aluminum compound, the aluminum metal and/or the aluminum compound is deemed an aluminum metal and/or an aluminum compound added to the reaction system according to this invention.

The process of this invention is carried out in the presence of water. The use of water has a merit that the amino alcohol can uniformly be reacted with the alkali metal hydroxide and/or the alkaline earth metal hydroxide, and is inevitable for obtaining the aminocarboxylic acid salt in high yield. The amount of water used in the reaction is 10% by weight or more, preferably 50 to 500% by weight based on the weight of the amino alcohol.

The reaction temperature is usually 220° C. or lower, preferably 120° to 210° C., most preferably 140° to 200° C. in order to prevent thermal decomposition and hydrogenolysis of a carbon-nitrogen bond of the amino alcohol and the resulting aminocarboxylic acid.

The reaction pressure is preferably as low as possible from the aspect of a reaction rate. It is usually more than the minimum pressure to advance the reaction in a liquid phase, preferably 5 to 50 kg/cm$^2$G.

The reaction can be carried out batchwise, semi-batchwise or continuously.

By separating the catalyst via filtration from the reaction mixture after the reaction is over, the aqueous solution of the intended aminocarboxylic acid salt is obtained as a filtrate. It is properly purified as required, thereby obtaining a high-quality amino-carboxylic acid salt as a product. On the other hand, the catalyst separated by filtration can be recovered and reused as such in the next reaction. Of course, the recovered catalyst may be used by proper regeneration treatment as required.

EFFECTS OF THE INVENTION

According to this invention, the aluminum metal and/or the aluminum compound is added to the reaction system in oxidatively dehydrogenating the amino alcohol in the presence of the alkali metal hydroxide and/or the alkaline earth metal hydroxide, the copper-containing catalyst and water, with a result that the intended aminocarboxylic acid salt can be produced in high yield with high selectivity.

The process of this invention can effectively suppress by-products remarkably especially when recovering the catalyst and repeatedly using it in comparison to the conventional processes wherein the aluminum metal or the aluminum compound is not added to the reaction system. Thus, in accordance with the process of this invention, the recovered catalyst can be circulated and reused without the regenerating treatment in most cases considerably reducing the cost of the catalyst, purification of the intended aminocarboxylic acid salt becomes easy, the amounts of the waste matters are decreased, and the high-quality product can be supplied inexpensively.

The process of this invention can also be carried out using a copper-containing catalyst recovered from the reaction mixture obtained by the conventional process in which the aluminum metal or the aluminum compound is not added to the reaction system. In this instance, by-products can be suppressed too.

BEST MODE TO WORK THE INVENTION

This invention is illustrated by the following Examples. However, this invention is not limited Conversion of the amino alcohol and selectivity to the aminocarboxylic acid are calculated by the following equations.

Conversion (%) of the amino alcohol =

$$\frac{\text{Number of mols of reacted amino alcohol}}{\text{Number of mols of amino alcohol subjected to the reaction}} \times 100$$

Selectivity (%) to the aminocarboxylic acid =

$$\frac{\text{Number of mols of formed aminocarboxylic acid}}{\text{Number of mols of reacted amino alcohol}} \times 100$$

EXAMPLE 1

A 500 ml autoclave was charged with 80 g of diethanolamine, 64 g of sodium hydroxide, 170 g of water, g of developed Raney copper, and 0.13 g (corresponding to 0.054% by weight, as an aluminum atom, based on the weight of the amino alcohol) of sodium aluminate, and the atmosphere inside the autoclave was replaced thrice with a hydrogen gas. Then, the reaction was conducted at a temperature of 170° C. and a pressure of 10 kg/cm²G until occurrence of hydrogen was no longer observed. The time required for the reaction (a time that lapsed from the temperature rise to 170° C. to the termination of the reaction—this is the same in the following) was 5 hours. After the reaction was over, the reaction solution was taken out and analyzed. As a result, conversion of diethanolamine was 98.5%, selectivity to sodium iminodiacetate was 99.3%, and selectivity to by-product sodium glycinate was 0.5%.

In order to measure repeated performance of the catalyst, the experiment was repeatedly conducted under the same reaction conditions. The reaction time required for the 10th repeated experiment was 13 hours. Analysis of the reaction solution revealed that conversion of diethanolamine was 98.5%, selectivity to sodium iminodiacetate was 98.7%, and selectivity to sodium glycinate was 1.0%.

COMPARATIVE EXAMPLE 1

The reaction was conducted as in Example 1 except that sodium aluminate was not used.

A 500 ml autoclave was charged with 80 g of diethanolamine, 64 g of sodium hydroxide, 170 g of water and 8 g of developed Raney copper, and the atmosphere inside the autoclave was replaced thrice with a hydrogen gas. The reaction was then conducted at a temperature of 170° C. and a pressure of 10 kg/cm²G until occurrence of hydrogen was no longer observed.

In order to measure repeated performance of the catalyst, the experiment was repeatedly conducted under the same reaction conditions. The reaction time required for the 10th repeated experiment was 13 hours. Analysis of the reaction solution revealed that conversion of diethanolamine was 97.5%, selectivity to sodium iminodiacetate was 93.5%, and selectivity to sodium glycinate was 5.8%.

EXAMPLE 2

A 500 ml autoclave was charged with 80 g of diethanolamine, 64 g of sodium hydroxide, 170 g of water, 8 g of developed Raney copper, and 0.12 g (corresponding to 0.052% by weight, as an aluminum atom, based on the weight of the amino alcohol) of aluminum hydroxide. After the atmosphere inside the autoclave was replaced thrice with a hydrogen gas, the reaction was conducted at a temperature of 170° C. and a pressure of 10 kg/cm²G until occurrence of hydrogen was no longer observed. The time required for the reaction was 5 hours. After the reaction was over, the reaction solution was taken out and analyzed. Consequently, conversion of diethanolamine was 98.5 %, selectivity to sodium iminodiacetate was 98.8 %, and selectivity to sodium glycinate was 0.8%.

In order to measure repeated performance of the catalyst, the experiment was repeatedly conducted under the same reaction conditions. The reaction time required for the 10th repeated experiment was 13 hours. Analysis of the reaction solution revealed that conversion of diethanolamine was 98.5%, selectivity to sodium iminodiacetate was 98.2%, and selectivity to sodium glycinate was 1.0%.

EXAMPLE 3

Sodium hydroxide was added to a solution obtained by dissolving 24.8 g of zirconium oxychloride and 4.0 g of copper nitrate in 300 ml of water to precipitate a solid insoluble matter. The precipitate was washed with water, dried, then heat treated in air at 500° C. for 3 hours, and reduced in a hydrogen stream at 230° C. for 6 hours to prepare a catalyst containing copper and zirconium.

A 500 ml autoclave was charged with 80 g of diethanolamine, 64 g of sodium hydroxide, 170 g of water, 8 g of the catalyst containing copper and zirconium which was prepared above, and 0.13 g (corresponding to 0.054 % by weight, as an aluminum atom, based on the weight of the amino alcohol) of sodium aluminate. The atmosphere inside the autoclave was replaced thrice with a hydrogen gas, and the reaction was then conducted at a temperature of 170° C. and a pressure of 10 kg/cm²G until occurrence of hydrogen was no longer observed. The time required for the reaction was 5 hours. After the reaction was over, the reaction solution was taken out and analyzed. Consequently, conversion of diethanolamine was 99.0%, selectivity to sodium iminodiacetate was 99.5%, and selectivity to sodium glycinate was 0.4%.

In order to measure repeated performance of the catalyst, the experiment was repeatedly conducted under the same reaction conditions. The reaction time required for the 10th repeated experiment was 10 hours after the temperature rise. Analysis of the reaction solution revealed that conversion of diethanolamine was 98.5%, selectivity to sodium iminodiacetate was 99.0%, and selectivity to sodium glycinate was 0.8%.

COMPARATIVE EXAMPLE 2

Example 3 was repeated except that sodium aluminate was not used.

Sodium hydroxide was added to a solution obtained by dissolving 24.8 g of zirconium oxychloride and 4.0 g of copper nitrate in 300 ml of water to precipitate a solid insoluble matter. The precipitate was washed with water, dried, then heat-treated in air at 500° C. for 3 hours, and reduced at 230° C. for 6 hours in a hydrogen stream to prepare a catalyst containing copper and zirconium. Eight grams of this catalyst were charged into a 500 ml autoclave together with 80 g of diethanolamine, 64 g of sodium hydroxide and 170 g of water, and the atmosphere inside the autoclave was replaced thrice with a hydrogen gas. The reaction was then conducted at a temperature of 170° C. and a pressure of 10 kg/cm²G until occurrence of hydrogen was no longer observed.

In order to measure repeated performance of the catalyst, the experiment was repeatedly conducted under the same reaction conditions. The reaction time required for the 10th repeated experiment was 10 hours after the temperature rise. Analysis of the reaction solution revealed that conversion of diethanolamine was 97.5%, selectivity to sodium iminodiacetate was 95.0%, and selectivity to sodium glycinate was 4.5%.

COMPARATIVE EXAMPLE 3

A 500 ml autoclave was charged with 80 g of diethanolamine, 64 g of sodium hydroxide, 170 g of water and 8 g of developed Raney copper, and the atmosphere inside the autoclave was replaced thrice with a hydrogen gas. The reaction was then carried out at a temperature of 170° C. and a pressure of 10 kg/cm²G until occurrence of hydrogen was no longer observed. The catalyst was repeatedly used. Analysis of the reaction solution in the 3rd repeated experiment revealed that conversion of diethanolamine was 98.5%, selectivity to sodium iminodiacetate was 96.5%, and selectivity to sodium glycinate was 3.0%.

EXAMPLE 4

The experiment was further conducted using the catalyst 10 times as in Comparative Example 3 except that developed Raney copper recovered from the reaction solution in the 3rd repeated experiment in Comparative Example 3 was used and 0.10 g (corresponding to 0.025% by weight, as an aluminum atom, based on the weight of amino alcohol) of aluminum chloride was added each time. The reaction time required for the 10th repeated experiment was 13 hours. Analysis of the reaction solution revealed that conversion of diethanolamine was 98.5%, selectivity to sodium iminodiacetate was 98.5%, and selectivity to sodium glycinate was 1.3%.

EXAMPLE 5

A 500 ml autoclave was charged with 80 g of diethanolamine, 64 g of sodium hydroxide, 170 g of water, 16 g of developed Raney copper and 0.024 g (corresponding to 0.010% by weight, as an aluminum atom, based on the weight of the amino alcohol) of sodium aluminate, and the atmosphere inside the autoclave was replaced thrice with a hydrogen gas. The reaction was then carried out at a reaction temperature of 160° C. and a reaction pressure of 10 kg/cm²G until occurrence of hydrogen was no longer observed. The time required for the reaction was 5 hours after the temperature was raised to 160° C. After the reaction was over, the reaction solution was taken out and analyzed. As a result, conversion of diethanolamine was 98.5%, selectivity to sodium iminodiacetate was 99.1, and selectivity to by-product sodium glycinate was 0.5%.

In order to measure repeated performance of the catalyst, the experiment was repeatedly conducted under the same reaction conditions. The reaction time required for the 10th repeated experiment was 13 hours after the temperature rise.

After the 10th reaction was over, the reaction solution was taken out and analyzed. Consequently, conversion of diethanolamine was 99.0%, selectivity to sodium iminodiacetate was 98.4, and selectivity to byproduct sodium glycinate was 1.4%.

EXAMPLE 6

A 500 ml autoclave was charged with 84 g of monoethanolamine, 61 g of sodium hydroxide, 132 g of water, 17 g of developed Raney copper, and 0.035 g (corresponding to 0.014% by weight, as an aluminum atom, based on the weight of the amino alcohol), and the atmosphere inside the autoclave was replaced thrice with a hydrogen gas. The reaction was then carried out thrice at a reaction temperature of 160° C. and a reaction pressure of 10 kg/cm²G until occurrence of hydrogen was no longer observed. The time required for the reaction was 4 hours after the temperature was raised to 160° C. After the reaction was over, the reaction solution was taken out and analyzed. As a result, conversion of monoethanolamine was 99.8%, selectivity to sodium glycinate was 99.4%, and selectivity to by-product sodium oxalate was 0.6%. In order to measure repeated performance of the catalyst, the experiment was repeatedly conducted under the same reaction conditions. The reaction time required for the 10th repeated experiment was 5 hours after the temperature rise.

After the reaction was over, the reaction solution was taken out and analyzed. As a result, conversion of monoethanolamine was 99.5%, selectivity to sodium glycinate was 99.3%, and selectivity to byproduct sodium oxalate was 0.7%.

COMPARATIVE EXAMPLE 4

Example 5 was repeated except that sodium aluminate was not used.

A 500 ml autoclave was charged with 84 g of monoethanolamine, 61 g of sodium hydroxide, 132 g of water and 17 g of developed Raney copper, and the atmosphere inside the autoclave was replaced thrice with a hydrogen gas. The reaction was then conducted at a reaction temperature of 160° C. and a reaction pressure of 10 kg/cm²G until occurrence of hydrogen was no longer observed. In order to measure repeated performance of the catalyst, the experiment was repeated under the same reaction conditions. The reaction time required for the 10th repeated experiment was 5 hours after the temperature rise.

After the reaction was over, the reaction solution was taken out and analyzed. As a result, conversion of monoethanolamine was 98.3%, selectivity to sodium glycinate was 96.0% and selectivity to by-product sodium oxalate was 3.5%.

EXAMPLE 7

A 500 ml autoclave was charged with 58 g of triethanolamine, 51 g of sodium hydroxide, 170 g of water, 17 g of developed Raney copper and 0.035 g (corresponding to 0.020% by weight, as an aluminum atom, based on the weight of the amino alcohol) of sodium aluminate, and the atmosphere inside the autoclave was replaced thrice with a hydrogen gas, and the reaction was then conducted at a reaction temperature of 190° C. and a reaction pressure of 10 kg/cm²G until occurrence of hydrogen was no longer observed. The time required for the reaction was 7 hours after the temperature was raised to 190° C. After the reaction was over, the reaction solution was taken out and analyzed. As a result, conversion of triethanolamine was 99.8%, selectivity to sodium nitrilotriacetate was 97.2%, and selectivity to by-product sodium iminodiacetate was 1.5%. In order to measure repeated performance of the catalyst, the experiment was repeatedly conducted under the same reaction conditions. The reaction time required for the 10th repeated experiment was 15 hours after the temperature rise.

After the reaction was over, the reaction solution was taken out and analyzed. As a result, conversion to triethanolamine was 99.5%, selectivity to sodium nitrilotriacetate was 94.3%, and selectivity to by-product sodium iminodiacetate was 4.0%.

COMPARATIVE EXAMPLE 5

The reaction was conducted as in Example 5 except that sodium aluminate was not used.

A 500 ml autoclave was charged with 58 g of triethanolamine, 51 g of sodium hydroxide, 170 g of water, and 17 g of developed Raney copper, and the atmosphere inside the autoclave was replaced thrice with a hydrogen gas. The reaction was then carried out at a reaction temperature of 190° C. and a reaction pressure of 10 kg/cm$^2$G until occurrence of hydrogen was no longer observed. In order to measure repeated performance, the experiment was repeatedly conducted under the same reaction conditions. The reaction time required for the 10th repeated experiment was 15 hours after the temperature rise.

After the reaction was over, the reaction solution was taken out and analyzed. As a result, conversion of triethanolamine was 98.5%, selectivity to sodium nitrilotriacetate was 90.5%, and selectivity to by-product sodium iminodiacetate was 7.5%.

We claim:

1. A process for producing an aminocarboxylic acid salt by an oxidative dehydrogenation reaction of an amino alcohol represented by formula (1)

$$\begin{array}{c} R^1 \\ \phantom{R^1}\diagdown \\ \phantom{R^1R^1}N-CH_2CH_2OH \\ \phantom{R^1}\diagup \\ R^2 \end{array} \quad (1)$$

wherein $R^1$ and R2, independently from each other, denote a hydrogen atom, a hydroxyethyl group, an alkyl group having 1 to 18 carbon atoms, or an aminoalkyl group having 2 to 3 carbon atoms, in the presence of an alkali metal hydroxide and/or an alkaline earth metal hydroxide, a copper-containing catalyst and water, characterized in that the reaction is carried out by adding an aluminum metal and/or an aluminum compound to the reaction system.

2. The process of claim 1 wherein 0.001% by weight or more, as an aluminum atom, based on the weight of the amino alcohol, of an aluminum metal and/or an aluminum compound is added to the reaction system.

3. The process of claim 1 or 2 wherein the copper-containing catalyst after used in the reaction is recovered and reused in the next reaction.

* * * * *